United States Patent [19]
Boyer et al.

[11] Patent Number: 5,271,405
[45] Date of Patent: Dec. 21, 1993

[54] WRIST MOUNT APPARATUS FOR USE IN BLOOD PRESSURE TONOMETRY

[76] Inventors: Stanley J. Boyer, 2320 Presidio Dr., San Diego, Calif. 92103; Stephen A. Martin, 2812 Sombrosa St., Carlsbad, Calif. 92009; Christine A. Giurdanella-Renzi, 8279 Torero Pl., San Diego, Calif. 92126; Charles R. Holdaway, 7242 Alliance Ct., San Diego, Calif. 92119; Robert D. Butterfield, 13980 Poway Valley Rd., Poway, Calif. 92064

[21] Appl. No.: 699,859

[22] Filed: May 14, 1991

[51] Int. Cl.$^5$ .................................................. A61B 5/00
[52] U.S. Cl. ................................... 128/672; 128/690
[58] Field of Search .............. 128/672, 677, 680–683, 128/686–687, 689–690, 661.08, 666–667

[56] References Cited

U.S. PATENT DOCUMENTS

| | | | |
|---|---|---|---|
| 3,090,377 | 5/1963 | Salisbury et al. | 128/677 |
| 3,099,262 | 7/1963 | Bigliano | 128/672 |
| 4,185,641 | 1/1980 | Minior et al. | 128/675 |
| 4,237,935 | 12/1980 | Delmonte et al. | 128/675 |
| 4,353,374 | 10/1982 | Nebbe et al. | 128/686 |
| 4,406,289 | 9/1983 | Wesseling et al. | 128/672 |
| 4,429,700 | 2/1984 | Thees et al. | 128/681 |
| 4,901,733 | 2/1990 | Kaida et al. | 128/672 |
| 4,993,422 | 2/1991 | Hon et al. | 128/672 |

FOREIGN PATENT DOCUMENTS 9002512  3/1990  World Int. Prop. O. .......... 128/672

*Primary Examiner*—William E. Kamm

[57] ABSTRACT

A wrist mount apparatus for placing a tissue stress sensor in operative engagement with the tissue overlaying an artery of interest is disclosed for use in a system for noninvasively determining the intra-arterial blood pressure of a patient. The wrist mount apparatus comprises a base portion and a transducer platform which is pivotally and slidingly engaged to the base portion. This arrangement allows the apparatus to be used on either the right or the left wrist of the wearer. A force overload system is provided whereby the wearer is protected from excessive forces applied to the wrist tissue by the apparatus used to applanate the artery. A quick disconnect feature allows the tissue stress sensor to be removed from the wrist mount apparatus without necessitating the use of tools. A disposable, anticontamination film is used with each application of the wrist mount apparatus to minimize the risk of transferring contaminants from one wearer to another and to prevent a build up of materials on the sensor's face.

17 Claims, 7 Drawing Sheets

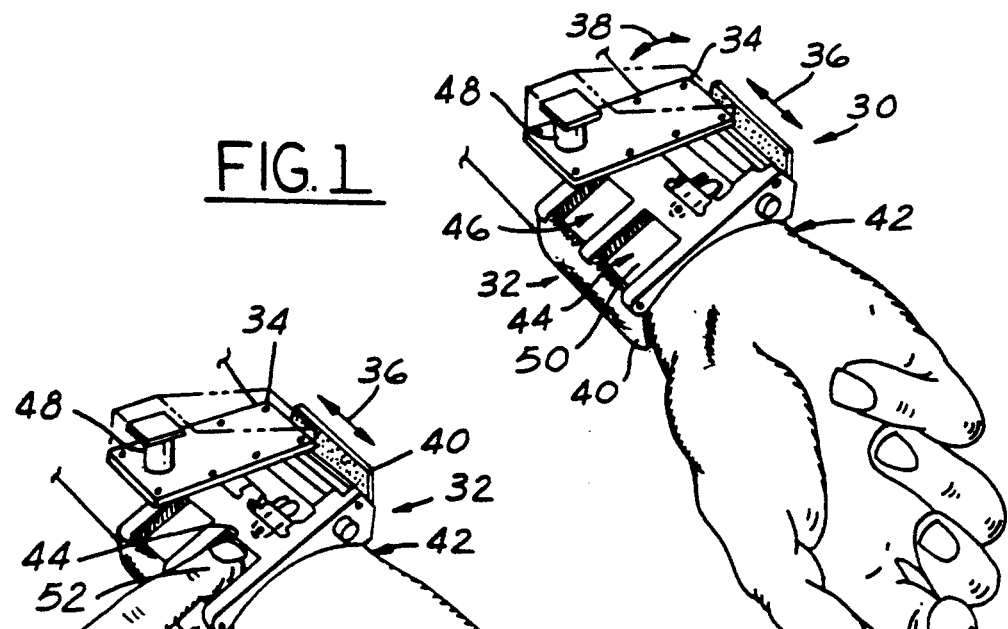
FIG. 1
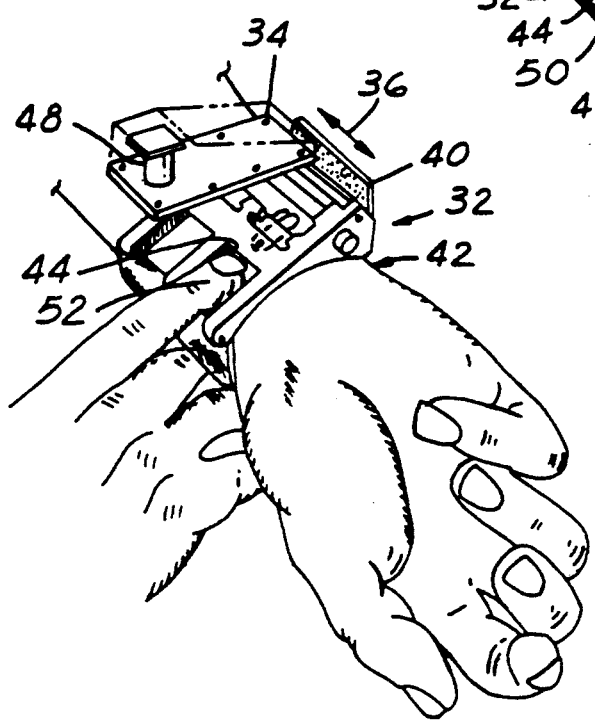
FIG. 2
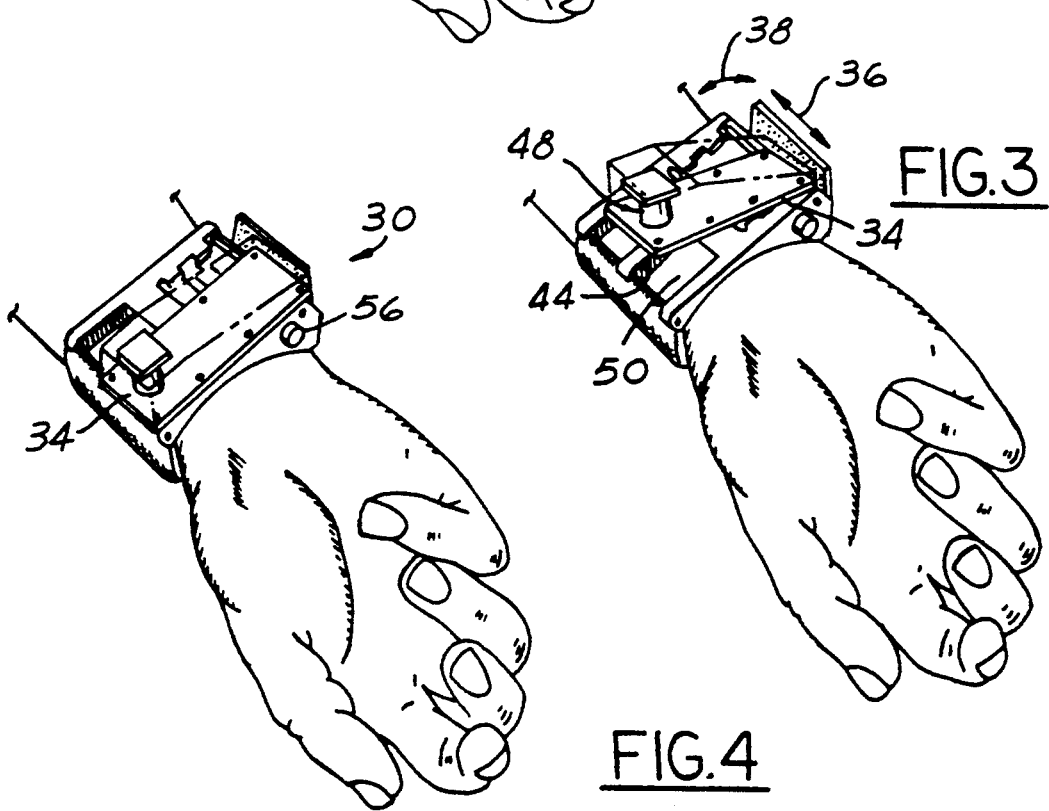
FIG. 3
FIG. 4

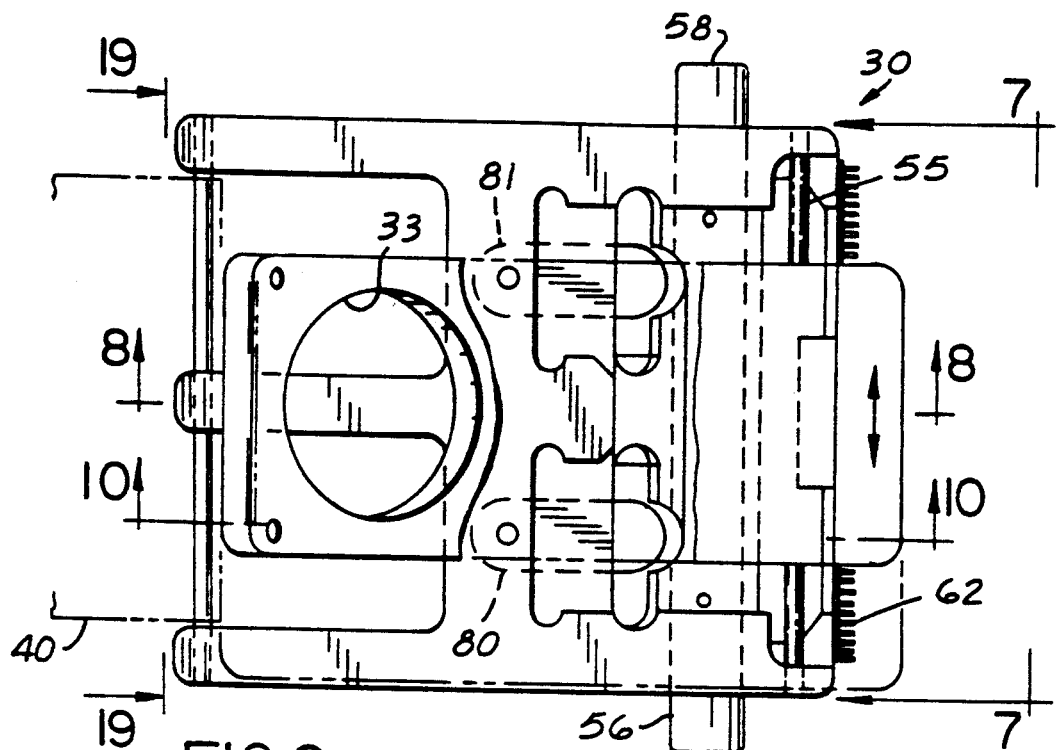
FIG.6
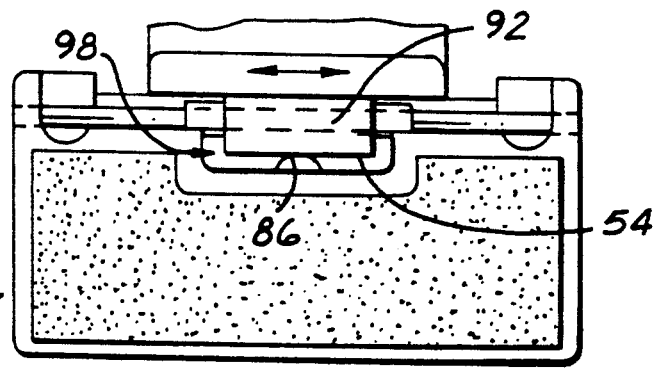
FIG.7
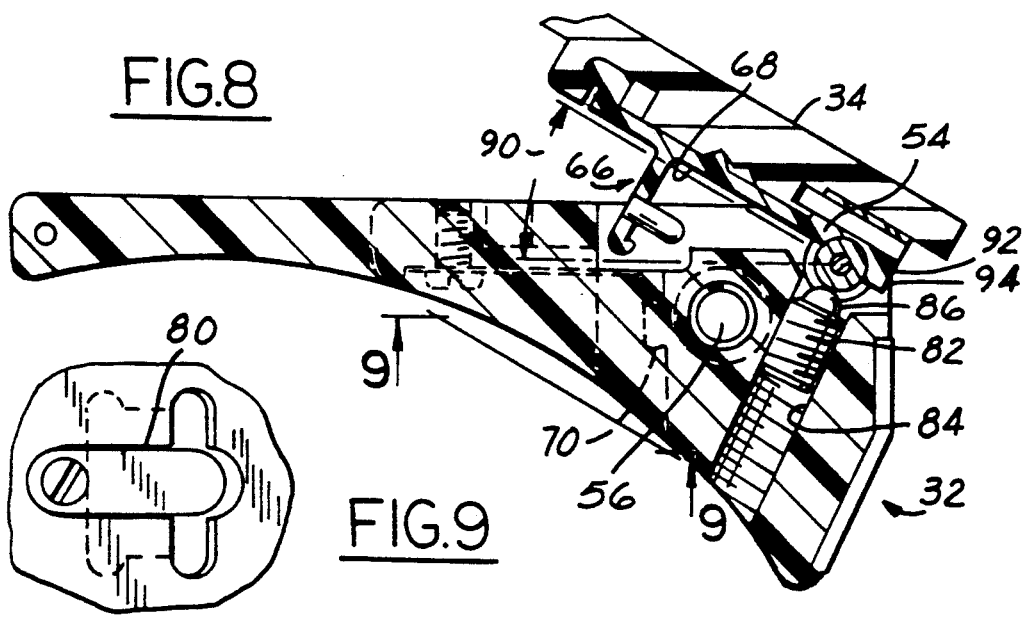
FIG.8
FIG.9

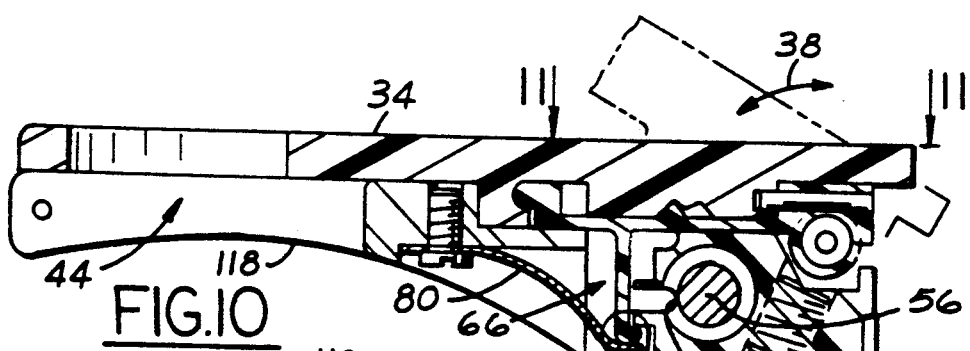
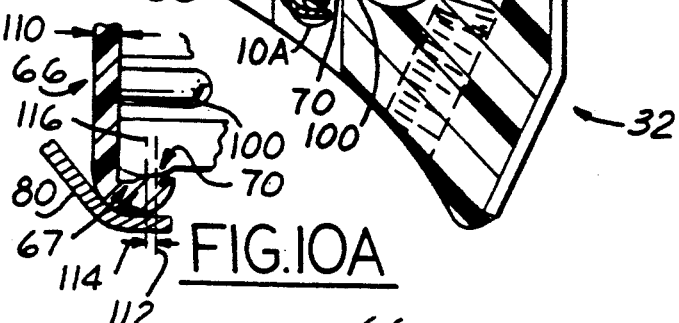
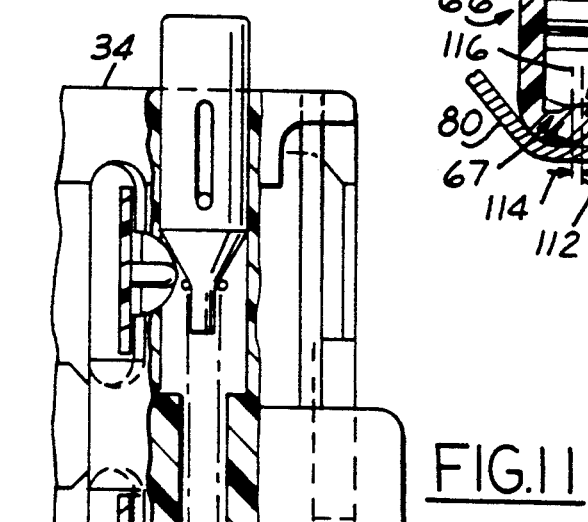
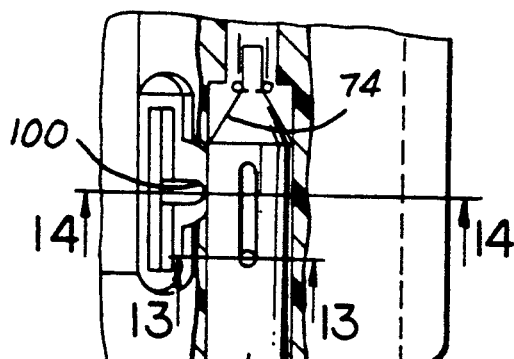
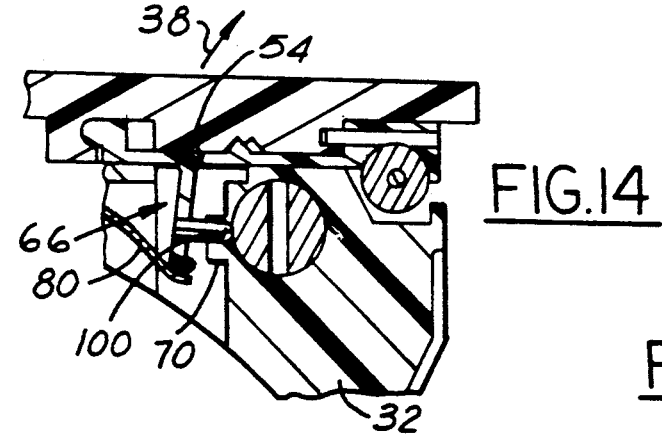
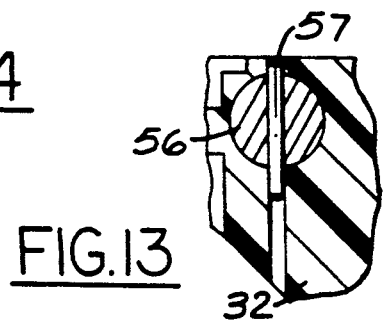

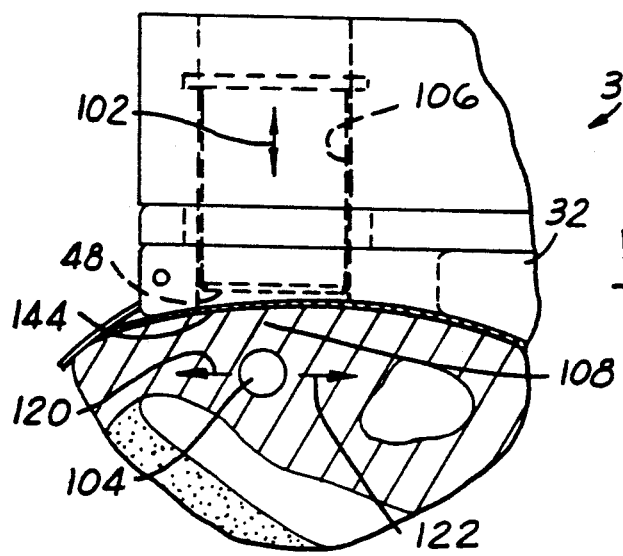
FIG.20
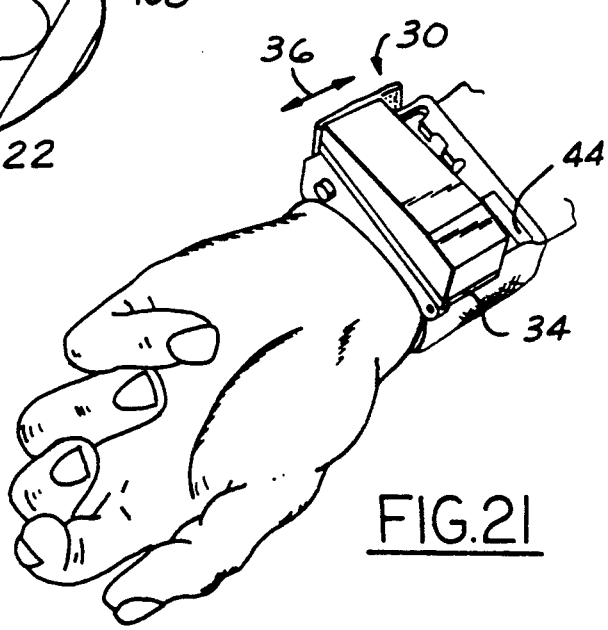
FIG.21
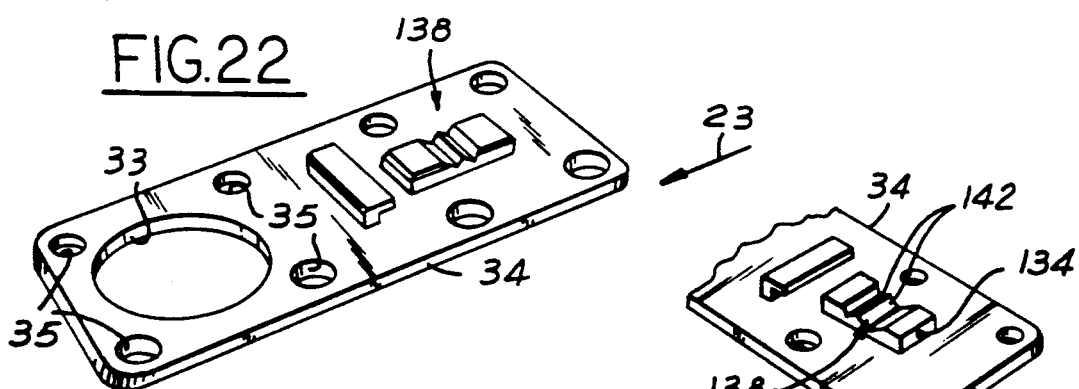
FIG.22
FIG.23
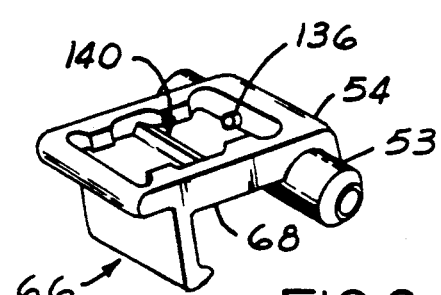
FIG.24

WRIST MOUNT APPARATUS FOR USE IN BLOOD PRESSURE TONOMETRY

TECHNICAL FIELD

The present invention generally relates to blood pressure tonometry, and more particularly relates to a wrist mount apparatus for use with a tissue stress sensor.

BACKGROUND OF THE INVENTION

Systems for measuring the intra-arterial blood pressure of a patient can be subdivided into two main groups—those which invade the arterial wall to access blood pressure and those which use noninvasive techniques. Initially, the most accurate blood pressure measurements were achievable only by way of invasive methods. One common invasive method involves inserting a fluid filled catheter into the patient's artery.

While invasive methods provide for accurate blood pressure measurements, the associated risk of infection and potential for complications, in many cases, outweigh the advantages in using invasive methods. Because of these risks associated with invasive methods, a noninvasive method, known as the Korotkoff method is widely used.

The Korotkoff method is known as an auscultatory method because it uses the characteristic sound made as the blood flows through the artery to mark the points of highest (systolic) and lowest (diastolic) blood pressure. Although the Korotkoff method is noninvasive, it only provides a measurement of the highest pressure and the lowest pressure along the continuous pressure wave. While systolic and diastolic pressure are sufficient for accurate diagnosis in many instances, there are many applications in which it is desirable to monitor and utilize the entire characteristic curve of the blood pressure wave. In these applications, the Korotkoff method simply is incapable of providing ample information. In addition to this limitation of the Korotkoff method, it necessitates the temporary occlusion of the artery in which blood pressure is being monitored. While arterial occlusion is not prohibitive in many applications, there are occasions where the patient's blood pressure must be monitored continuously (such as when undergoing surgery) and accordingly, the prohibiting of blood flow, even on a temporary basis, is undesirable.

Because of the above-mentioned risks involved with invasive blood pressure measurement, and the shortcomings of the Korotkoff method, extensive investigation has been conducted in the area of continuous, noninvasive blood pressure monitoring and recording. Some of these noninvasive techniques make use of tonometric principles which take advantage of the fact that as blood pressure flows through the arterial vessel, forces are transmitted through the artery wall and through the surrounding arterial tissue and are accessible for monitoring at the surface of the tissue. Because the tonometric method of measuring blood pressure is noninvasive, it is used without the risks associated with invasive techniques. Furthermore, in addition to being more accurate than the Korotkoff method discussed above, it has the capability of reproducing the entire blood pressure wave form, as opposed to only the limited systolic and diastolic pressure points provided by the Korotkoff method.

Because the accuracy of tonometric measurements depends heavily upon the method and apparatus used to place and maintain the sensor against the tissue overlying the artery of interest, several apparatuses have been specifically developed for this purpose. For example, U.S. Pat. No. 4,784,152 issued to Shinoda, et al. on Nov. 15, 1988 discloses a sensor positioning device which is capable of moving a contact sensor relative to and along the surface of a patients body tissue. A pressing device is provided for moving each contact element relative to the main frame, in a direction toward the tissue, for forcing each sensor against the tissue. Likewise, U.S. Pat. No. 4,947,855 issued to Yokoe, et al. on Aug. 14, 1990 discloses a blood pressure measuring apparatus having a housing detachably set on a body surface of a subject. A pressure sensor is accommodated in the housing such that the pressure sensor is opposed to the body surface when the housing is set on the body surface, the pressure sensor being pressed against the body surface so as to detect pulse waves produced from an arterial vessel of the subject. Also, in U.S. Pat. No. 4,966,156 issued to Perry, et al., a pressurization system for continuous blood pressure monitoring is disclosed comprising a dual chamber compression apparatus and switching mechanism, both of which are engaged to a servo motor drive mechanism. The drive mechanism simultaneously controls the compression apparatus and the switching mechanism thereby coordinating flow of air from the compression chamber to the pressurizable chamber within the transducer.

It can be seen, in conjunction with the above-mentioned patents, that they possess several drawbacks. Firstly, they do not possess the means for releasing the pressure applied by the pressure sensing head in the event that the pressure applied becomes excessive (such as in a malfunction condition). Secondly, the construction of the above-discussed systems is not modular and accordingly, the majority of its components are not field serviceable. Thirdly, it is evident from the above systems, that because they directly contact the skin of the wearer, any contaminants thereon is transferred to the sensing head thereby contaminating the head, and possibly being transferred to a subsequent wearer. Lastly, by way of general observation, the above-discussed systems are generally bulky, and accordingly, are cumbersome to use and operate. Moreover, the above systems are designed to be universally applicable for either right or left wrist usage. Because they are designed with this universality in mind, they are unable to take advantage of specific wrist characteristics when, properly taken advantage of, can provide a more stable platform to thereby engage and operate the tissue stress transducer.

Thus, it is desirable to provide a wrist mount apparatus for use in blood pressure tonometry wherein various wrist characteristics are taken advantage of to provide a single sensor which can universally adapt to the right or left wrist and accordingly, provide a secure platform to thereby mount a tissue stress sensor upon.

It is also an object of this invention to provide a force overload release system whereby the risk of damage to the tissue of a wearer is minimized should the device fail and attempt to apply excessive force to the wearers wrist area.

It is also an object of this invention to provide a quick disconnect system whereby the tissue stress sensor may be quickly removed from the wrist mount apparatus thereby making the entire assembly less costly to service and also allowing the wrist mount apparatus to be field serviceable and even disposable.

It is still an additional feature of this invention to provide a wrist mount apparatus which minimizes the risk that contaminants will be passed from wearer to wearer or from a wearers wrist to the tissue stress sensor head.

Yet still it is an object of the present invention to provide a wrist mount apparatus which assists an operator in quickly and easily locating an artery of interest while also acting to stabilize the artery thereby reducing its tendency to move or roll.

SUMMARY OF THE INVENTION

In light of the foregoing objects, the present invention provides a wrist mount apparatus for use in a system for noninvasively determining the intra-arterial blood pressure of a wearer. The wrist mount apparatus places a tissue stress transducer in operative engagement with the tissue overlying an artery of interest. The wrist mount apparatus comprises a base portion which is adapted to be mounted to the wrist of a wearer and a transducer platform adapted to house the tissue stress transducer. The transducer platform is pivotally and slidably mounted to the base portion such that when the wrist mount apparatus is mounted to the right wrist of the wearer, the transducer platform can be slid into a use position and is thereby operative for allowing the transducer platform to be pivoted into operative engagement with the tissue overlying an artery of interest. When the wrist mount apparatus is mounted to the left wrist of the wearer, the transducer platform is slidable to a second position wherein it allows the tissue stress transducer to pivot into operative engagement with the tissue overlaying an artery of interest, whereby the apparatus is adapted for use on the right or left wrist of the wearer.

Preferably the base portion includes first and second window portions, whereby the first window portion is placed over the artery of interest when the apparatus is placed on the right wrist of the wearer and the second window is placed over the artery of interest when the apparatus is placed on the left wrist of the wearer. The window portions are preferably large enough to permit the finger of an operator to pass therethrough for the purpose of palpating the artery of interest.

The wrist mount apparatus preferably includes locking means for locking the base portion to the transducer platform thereby preventing the platform from freely pivoting when the apparatus is in use. Release means are provided to release the transducer platform from the lock position when it is desirable to move the tissue stress sensor to a different position or to manually palpate the artery of interest to ensure that the wrist mount apparatus is properly positioned on the wearer's wrist.

The base portion of the mounting apparatus has a wrist engaging surface wherein the wrist engaging surface is generally concave to generally conform the base to the natural curvature of the wearers wrist. This promotes general wearer comfort as well as stability of the base on the wearer's wrist. Additionally, the concave surface tends to stabilize the artery of interest against moving or rolling. Thus, the artery of interest is stabilized and has less of a tendency to move once pressure is applied to it by the tissue stress sensor than it otherwise would in applications where the wrist engaging surface of the base portion is flat or non-concave. Additional stability is also provided by virtue of a rib disposed between adjacent windows.

In addition to allowing the tissue stress sensor to move between a first and second position to accommodate the right hand and left hand use of the wrist mount apparatus, a third position is provided whereby the tissue stress sensor is pivotal away from the base portion in sufficient displacement so as to make the tissue stress sensor accessible for calibration without necessitating its removal from the apparatus. The third position is also effective for making sensor easier to service or remove.

In another aspect, the apparatus of the present invention sets forth a wrist mount apparatus comprising a base portion adapted to be mounted to the wrist of a wearer, a transducer platform adapted to house the tissue stress transducer, wherein the transducer platform is movably engaged to the base portion, means coupled between the transducer platform and the tissue stress transducer for placing the tissue stress transducer into operative engagement with the tissue overlying the artery of interest, and means, coupled between the base portion and the transducer platform, for releasing the tissue stress transducer from operative engagement with the tissue overlying the artery of interest. The releasing means is operative whenever the force of the tissue stress transducer against the tissue of the wearer exceeds a predetermined value. The releasing means preferably includes a resilient engaging finger extending from the transducer platform wherein the finger is adapted to engage an engaging surface on the base portion thereby retaining the transducer platform to the base portion and preventing, under normal operating conditions, any relative movement between the base portion and the transducer platform. When a force of sufficient urging is exerted by said tissue stress sensor against the tissue overlying the artery of interest, the resilient engaging finger is sufficiently distorted to disengage from the engaging surface of the base portion thereby allowing relative movement to take place between the base portion and the transducer platform. The resilient engaging finger preferably includes a concave engagement surface and of the engagement surface of the base portion is preferably generally concave. These two concave surfaces, when engaged with one another, are adapted to cooperate thereby retaining the resilient engaging finger to the base portion engagement surface when the force between them is less than a predetermined value and wherein the resilient engaging finger quickly releases from the base portion engagement surface when the force between them is greater than a predetermined value.

Still, in another aspect, the apparatus of the present invention provides a wrist mount apparatus comprising a base portion adapted to be mounted to the wrist of a wearer, a transducer platform adapted to engage a tissue stress transducer, and a quick disconnect means for connecting the transducer platform to the base portion whereby the disconnect means allows the transducer platform and the tissue stress sensor to be quickly removed from the base portion. The quick disconnect means preferably includes a coupling member fastened to the base portion wherein the coupling member includes a lip portion and the transducer platform includes a recess portion wherein the lip portion is adapted to slidingly engage and retain the recessed portion.

Still, in another aspect, the wrist mount apparatus of the present invention includes a base portion adapted to be mounted to the wrist of a wearer and a transducer platform adapted to house the tissue stress transducer, wherein the transducer platform is engaged to the base portion. Means is disposed between the tissue stress sensor and the tissue overlying an artery of interest for preventing direct contact between the tissue stress sensor and the tissue whereby the sensor face is not contaminated by elements disposed on the tissue of the wearer. Preferably, preventing means includes a thin film of plastic.

Other advantages and meritorious features of the present invention will become more fully understood from the following description of the preferred embodiments, the appended claims and the drawings, a brief description of which follows.

BRIEF DESCRIPTION OF THE DRAWINGS

FIG. 1 is a perspective view of the wrist mount apparatus of the present invention as it is oriented on a wearers wrist.

FIG. 2 is a perspective view of the wrist mount apparatus of the present invention wherein the wearers artery of interest is being palpated.

FIG. 3 is a perspective view of the wrist mount apparatus of the present invention wherein the transducer platform has been slid in position adjacent the artery of interest.

FIG. 4 is a perspective view of the wrist mount apparatus of the present invention wherein the transducer platform has been rotated and locked in position over an artery of interest.

FIG. 6 is a top view of the wrist mount apparatus of the present invention.

FIG. 7 is a rear side view of the wrist mount apparatus of the present invention taken substantially along lines 7—7 of FIG. 6.

FIG. 8 is a partial cross-sectional view of a wrist mount apparatus of the present invention taken substantially along lines 8—8 of FIG. 6.

FIG. 9 is a partial bottom view of the wrist mount apparatus of the present invention taken substantially along lines 9—9 of FIG. 8.

FIG. 10 is a partial cross-sectional view of the wrist mount apparatus of the present invention taken substantially along lines 10—10 of FIG. 6.

FIG. 10A is a partial enlarged view of the overload release mechanism of the present invention shown in an underloaded, or normal use, position.

FIG. 10B is a partial cross-sectional view of the overload finger of the present invention shown in an overloaded position.

FIG. 11 is a partial cross-sectional view of the wrist mount apparatus of the present invention taken substantially along lines 11—11 of FIG. 10.

FIG. 12 is a partial top view of the wrist mount apparatus of the present invention wherein the manual release button is engaged.

FIG. 13 is a partial cross-section of the mechanical release button of the present invention taken substantially along lines 13—13 of FIG. 12.

FIG. 14 is a partial cross-sectional view of the mechanical release button of the present invention taken substantially along lines 14—14 of FIG. 12.

FIG. 20 is a partial right side view of the wrist mount apparatus of the present invention taken substantially along lines 20—20 of FIG. 19.

FIG. 21 is a perspective view of the wrist mount apparatus of the present invention shown placed on the left hand wrist of a wearer.

FIG. 22 is a bottom perspective view of the transducer platform.

FIG. 23 is a partial perspective bottom view of the transducer platform of FIG. 22.

FIG. 24 is a perspective view of the coupling member.

DETAILED DESCRIPTION OF THE PREFERRED EMBODIMENTS

Figure 5A:
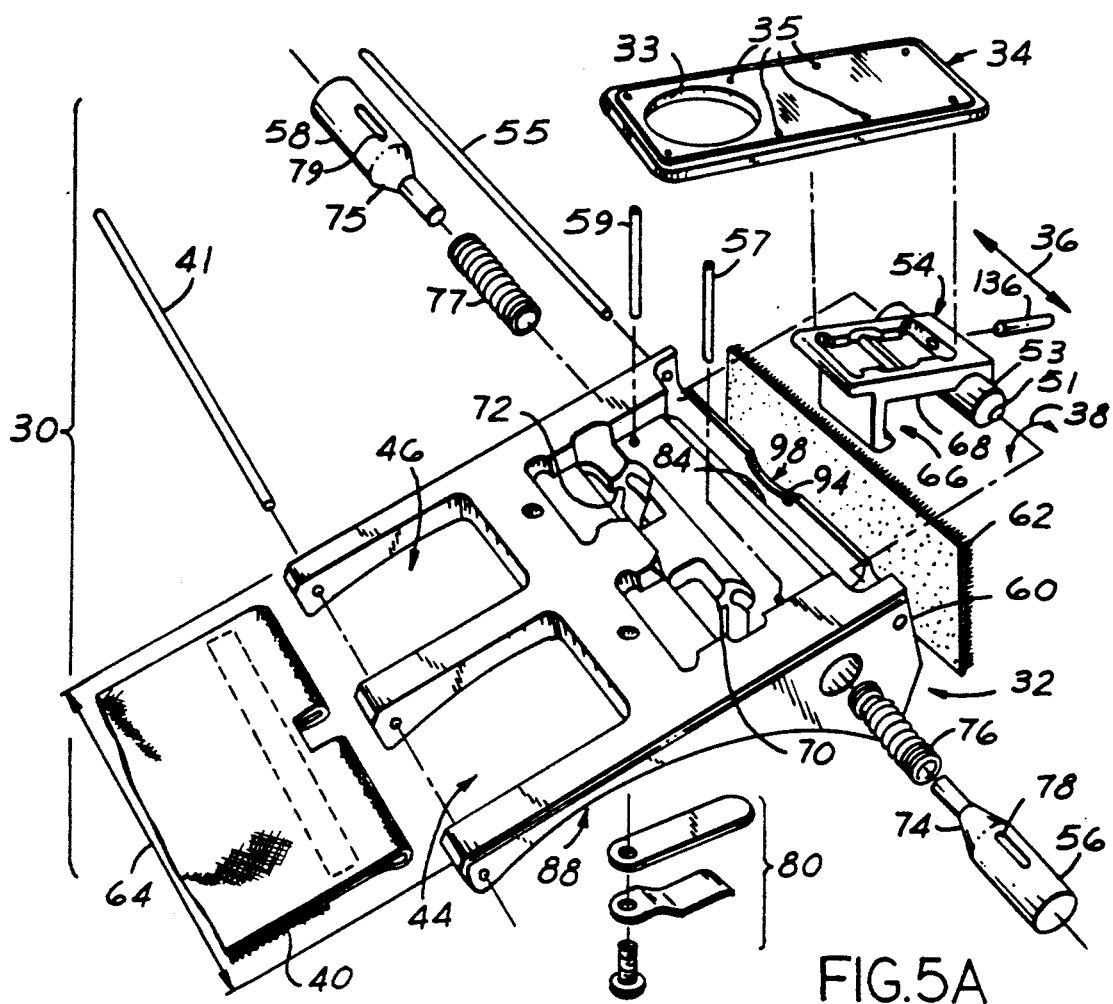
FIG. 5A is a perspective exploded top view of the wrist mount apparatus of the present invention.

Now referring to FIG. 1, wrist mount apparatus 30 generally comprises base portion 32 and transducer platform 34. Transducer platform is attached to base portion 32 in a way which allows platform 34 to move laterally 36 and pivotally 38. Base portion 32 includes restraining strap 40 for fixing base portion 32 to the wrist area 42 of a user. Base portion 32 includes first and second window 44, 46. When apparatus 30 is worn on the right wrist 42 of a user, platform 34 is moved laterally 36 so as to place tissue stress sensor 48 over window 44. Platform 34 is then pivoted downward towards wrist 42 so as to place stress sensor 48 in operative engagement with tissue 50 overlying an artery of interest. Similarly, when wrist mount apparatus 30 is placed on the left hand wrist of a user (as shown in FIG. 21), platform 34 is moved laterally 36 over window 46 and pivotally 38 such that tissue stress sensor 48 is centered within second window 46 thereby being placed in operative engagement with the tissue overlying the artery of interest. Thus, it can be seen, and will be more fully explained hereafter, that wrist mount apparatus 30 of the present invention is well suited to be used on either the right wrist or the left wrist of a wearer. It is important to note that although the preferred embodiment of sensor 48 is a tissue contact stress sensor as disclosed in copending patent application Ser. No. 07/500,063, the wrist apparatus of the present invention is capable of employing any sensor suitable for use in blood pressure tonometry. Accordingly, it is to be understood that although the use of tissue contact stress sensor, or tissue stress sensor is employed throughout this description, the wrist mount apparatus of the present invention is adapted to be used with any suitably designed senor.

Now referring to FIG. 2. When it is desired to use wrist mount apparatus 30 for placing tissue stress sensor 48 in operative engagement with the tissue overlaying an artery of interest, the following approach is used. Firstly, transducer platform 34 is moved laterally 36 such that first window 44 is generally unobstructed. Next, base portion 32 is placed on wrist 42 of the wearer such that first window 44 is generally centered upon the tissue overlaying the artery of interest. Once this initial positioning has occurred, restraining strap 40 is placed around the wrist thereby securing base portion 32 to wrist area 42. Next, the artery of interest is palpated 52 to ensure that the artery of interest properly lies within the area framed by first window 44. If no arterial pulse can be detected therein, strap 40 is released and window 44 is moved to a new location wherein palpation is attempted once more.

Now referring to FIG. 3, once window 44 is properly located over the artery of interest, platform 34 is moved laterally 36 such that tissue stress sensor 48 is generally above first window 44. Once this lateral movement 36 has been accomplished, platform 34 is pivoted 38 towards tissue 50 until platform 34 locks into its use position. Once this lateral 36 and pivotal 38 movement is accomplished, platform 34 is positioned over base portion 32 in the manner generally depicted in FIG. 4. In this position, wrist mount apparatus 30 is operative for use in a system for noninvasively determining the intra-arterial blood pressure of a wearer. Various features of wrist mount apparatus 30 will now be discussed, in detail, in conjunction with the remaining figures.

Now referring to FIG. 5A, base portion 32 is adapted to be fastened to the wrist of a wearer by way of strap 40. Strap 40 is fixed, at one end, to base portion 32 by way of strap pin 41. At its opposite end (not shown), strap 40 is fastened to surface 60 of base portion 32 which employs velcro 62, or some other suitable means for retaining strap 40. This, provides the primary means whereby base portion 32 is firmly secured to the wrist of a wearer thereby providing a secure foundation for mounting the remaining components of wrist mount apparatus 30. It is important to note, that the relatively wide width 64 of base 32, the curvature of wrist engaging surface 88 of base 32 and its relatively low profile all act to provide an excellent, stable base upon which a tissue stress sensor can operate.

Transducer platform 34 is adapted to engage, and be retained by, coupling member 54. The nature of this engagement is unique to the apparatus of the present invention and will be more fully explained in conjunction with subsequent drawings. However, it is important to note at this juncture, that the nature of the connection between platform 34 and coupling member 54 is one which can quickly be fastened, and unfastened, without using tools thereby making the disclosed system particularly attractive for replacing tissue stress sensors in the field. It also permits the face to remain in place on a wearer's wrist while replacing sensor 48.

Transducer platform 34 is fitted with a main aperture 33 and secondary apertures 35. Secondary apertures 35 provide a means of mounting a tissue stress sensor and its accompanying movement mechanism to transducer platform 34. Main aperture 33 provides a passageway whereby tissue stress sensor can pass through platform 34 and operatively engage the tissue overlying an artery of interest.

It is important to note that neither tissue stress sensor or apparatus associated therewith for affecting the movement of the tissue stress sensor is depicted in FIG. 5A of the drawings. Moreover, in the few drawings in which it is shown (FIGS. 1-4 and 19-21), it is depicted in a generic sense. This general approach is taken because the wrist mount apparatus of the present invention is not confined to any particular tissue stress sensor or, likewise, to any particular mechanism for effecting the movement of a tissue stress sensor. Accordingly, the wrist mount apparatus of the present invention can be used with any number of sensors, and movement mechanism, designs. Where it is informative to show the environment in which the wrist mount apparatus of the present invention operates, a generic tissue stress sensor and a generic movement mechanism is shown.

Transducer platform 34 mounts to coupling member 54 in a manner which will be more fully discussed hereinafter. Coupling retaining pin 55 acts to connect coupling member 54 to base portion 32 in a way which allows coupling member 54 to move both laterally 36 along pin 55 and pivotally 38 about pin 55. The lateral movement 36 allows platform 34 to engage either window 44, 46 for either right wrist use or left wrist use respectively.

Resilient engaging finger 66 extends from a bottom surface 68 of coupling member 54. Resilient engaging finger 66 is adapted to lock transducer platform 34 into its use position by contacting engagement surface 70, 72 when coupling member 54 is in the right hand use position, left hand use position respectively. Along with its engaging function, resilient engaging finger 66 also serves as an overload release member to prevent tissue damage from occurring in the event that the sensor movement mechanism malfunctions and attempts to apply excessive force to the wrist tissue of the wearer. This overload function will be described in greater detail in conjunction with the subsequent drawings.

Right wrist release button 56 is operative to release engagement finger 66 from engagement surface 70. Accordingly, after it is desired to pivot 38 platform 34 away from window 44 button 56 is depressed towards base portion 32 thereby causing conical surface 74 to engage resilient finger 66 and dislodge it from engagement surface 70 of base portion 32. Thus, it can be seen, that right wrist release button 56 releases transducer platform 34 from its positive engagement with base portion 32 thereby rendering it free to pivot 38. Right wrist release button 56 is fitted with a slotted aperture 78 which cooperates with retaining pin 57 to limit the inward and outward travel of button 56. Return spring 76 acts to keep right wrist release button 56 outwardly biased thereby urging it to return to its outwardly most bias position whenever a depression force is not placed on it. Thus, it can be seen, that right wrist release button 56 is operative to disengage finger 66 from engagement surface 70 of base portion 32 in the event that button 56 is depressed such that conical surface 74 engages and sufficiently displaces resilient finger 66. By analogy, it can be seen that whenever platform 34 is in the use position associated with the left wrist of a wearer, pin 59 cooperates with slotted aperture 79 of left wrist release button 58 to define its inward and outward allowable travel. Likewise, return spring 77 keeps left wrist release button 58 outwardly biased and conical surface 75 of left wrist release button 58 is adapted to engage finger 66 and displace it from engagement surface 72 of base portion 32 in a way which causes finger 66 to release its positive engagement with surface 72 thereby allowing transducer platform 34 to pivot 38.

Spring assembly 80 is operative to place a force of upward urging on finger 66 whenever finger 66 is engaged with surface 70 of base portion 32. Spring assembly 80 functions to ensure that coupling member 54 is rotated 38 away from engagement surface 70 whenever right wrist release button 56 is depressed. This rotation is generally desirable to ensure that platform 34 positively disengages from its use position whenever sufficient inward force is placed on release button 56. Without the upward biasing provided by spring assembly 80, an inward force on button 56, which is sufficient to disengage resilient finger 66 from engagement surface 70, would not fully release finger 66 from surface 70. This is because no other forces would be present to rotate 38 platform 34 away from window 44 and upon release of button 56, finger 66 would most likely reengage surface 70. Moreover, by not pushing coupling 54 upward, this would give the appearance that platform 34 was not yet released from engagement surface 70 causing excessive force to be applied to right release button 56. To avoid the use of excessive force, spring assembly 80 is provided to exert an upward force on finger 66 thereby causing transducer platform to "pop up" whenever right release button 56 is depressed with sufficient force. This pop up action makes it clear that finger 66 has positively disengaged from surface 70. A similar spring assembly is utilized on finger 66 when platform 34 is used in its left wrist use position.

Figure 5B:
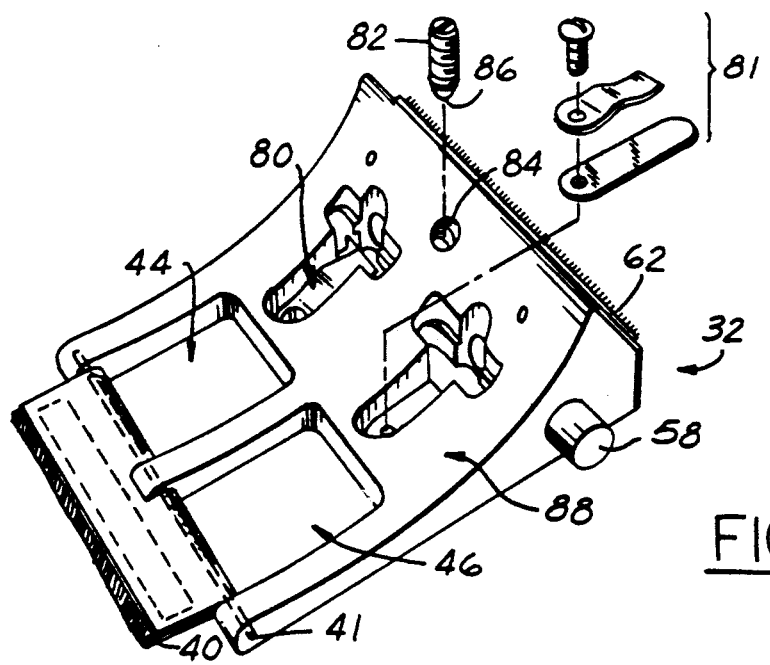
FIG. 5B is a perspective exploded bottom view of the wrist mount apparatus of the present invention.
Figure 15:
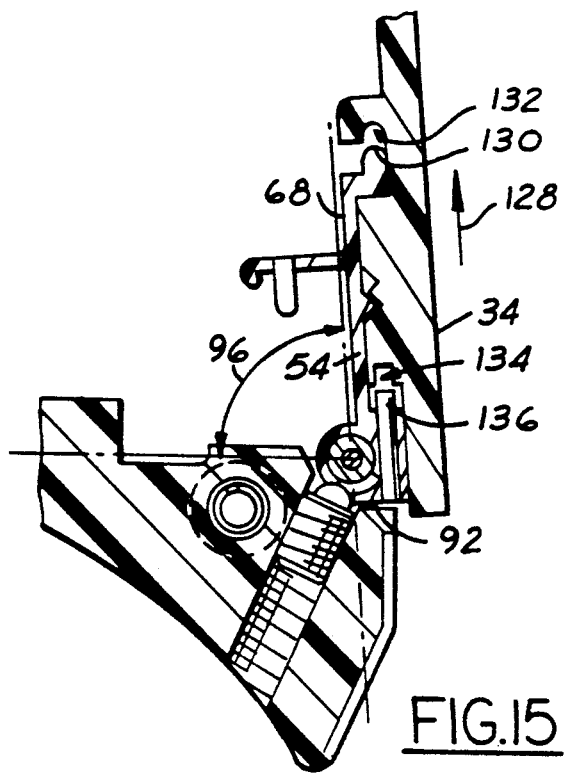
FIG. 15 is a partial cross-sectional view of the wrist mount apparatus of the present invention showing the slidable engagement between the transducer platform and the coupling member.
Figure 16:
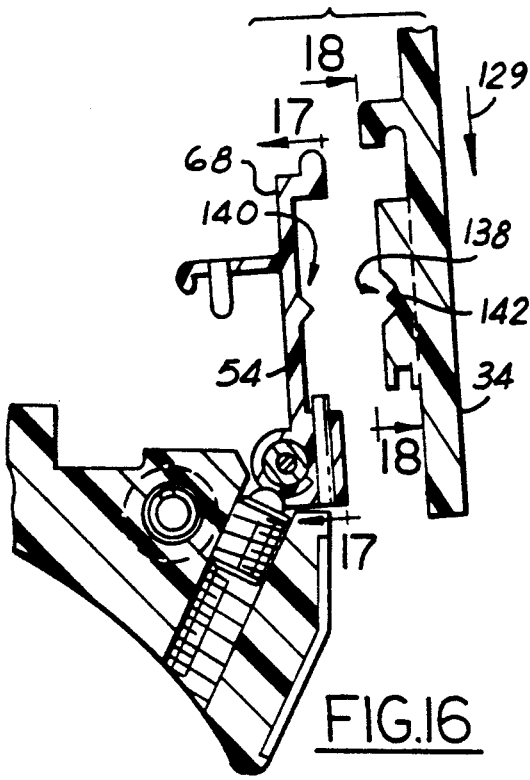
FIG. 16 is a cross-sectional view of the wrist mount apparatus of the present invention showing the transducer platform separated from the coupling member.
Figure 17:
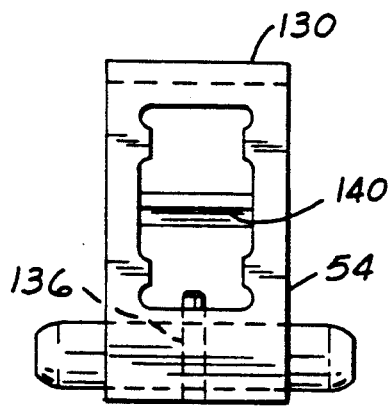
FIG. 17 is a top view of the coupling member taken substantially along lines 17—17 of FIG. 16.
Figure 18:
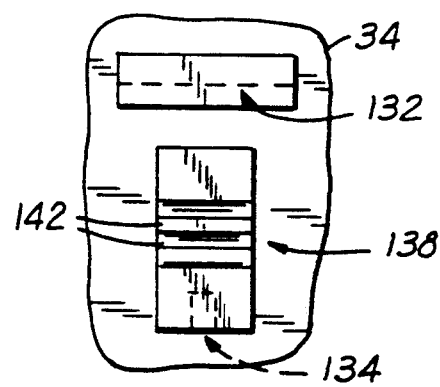
FIG. 18 is a bottom view of the transducer platform taken substantially along lines 18—18 of FIG. 16.
Figure 19:
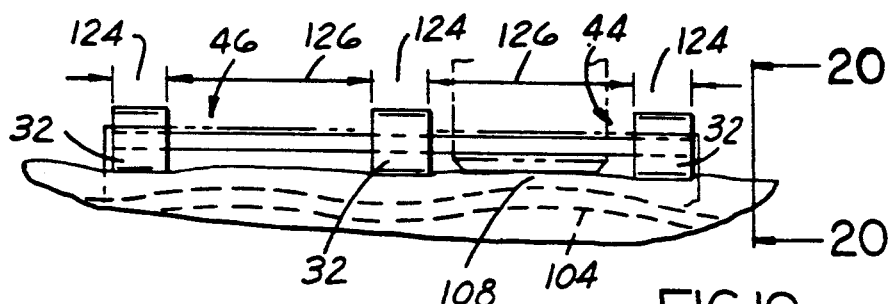
FIG. 19 is a front side view of the wrist mount apparatus of the present invention taken substantially along lines 19—19 of FIG. 6.

Now referring to FIG. 5B, a bottom view of base portion 32 shows spring assembly 81 which is associated with the use of wrist mount apparatus 30 when it is used on the left wrist of a wearer. Tension adjustment screw (or spring plunger) 82 is adapted to threadedly engage aperture 84 of base portion 32. Tension adjustment screw 82 is fitted with a spring loaded spherical-shaped end 86 which is adapted to frictionally engage barrel 53 of coupling member 54. This is generally desirable because as wrist mount apparatus 30 is used, barrel aperture 51 will begin to wear thereby allowing undesirable movement to take place between coupling member 54 and pin 55. If such wear should take place, the spring (spring not shown) within screw 82 is effective for maintaining an uninterrupted tension against barrel 53. If barrel or spherical end 86 wear beyond the ability of the spring within screw 82 to maintain tension against barrel 53, screw 82 is simply adjusted so that spherical end 86 once again places pressure on barrel 53 of coupling member 54 thereby eliminating any undesirable movement. In addition to the above mentioned tensioning function performed by tension adjustment screw 82, it also serves to locate and hold coupling member in the left, center or right hand position. For example, when coupling member 54 is in its central, raised position (see FIG. 15), a groove or depression centrally located in barrel 53 (groove or depression not shown) can engage spherical end 86 of screw 82 and maintaining coupling member 54 in its central position. Once a sufficient amount of lateral force is placed on coupling member 54, spherical end 86 of screw 82 will disengage from the central depression of barrel 53. Likewise, when coupling member 54 is moved into the left hand or right hand use position, barrel 54 can be appropriately sized such that spherical end 86 of screw 82 rides off of barrel 53 thereby maintaining coupling member in the left or right hand position. Thus, it can be seen, that the engagement of spherical end 86 of screw 82 in cooperation with barrel 53 of coupling member 54 is effective for maintaining coupling member 54 in a select number of lateral locations as coupling member 54 is laterally displaced along coupling pin 55.

SLIDABLE/PIVOTAL TRANSDUCER PLATFORM

FIGS. 1–8, 15, 16 and 21 will now be used to describe the slidable and pivotal aspect of platform 34 of the present invention. As can be seen in comparing FIG. 4 to FIG. 21, wrist mount apparatus 30 employs transducer platform 34 in a first use position when apparatus 30 is mounted to the right wrist of a user (see FIG. 4) and employs platform 34 in a second use position when apparatus 30 is mounted to the left wrist of a wearer (see FIG. 21). Because apparatus 30 must be adaptable to be used on either the right or the left wrist of a wearer, and also because contour 88 of base 32 (see FIG. 5B) is adapted to conform to the surface contour of a users wrist, base portion 32 must be flipped around when switched from opposite wrists. This switching is necessary in order to have contour 88 properly engage the natural contour of the wrist it is being used on. Because it is necessary to flip base 32 around, platform 34 must be movable laterally 36 so that tissue stress sensor 48 can always be placed in the window proximate the wearers fingers. For example, in FIG. 3, base 34 is positioned laterally 36 such that tissue stress sensor 48 is positioned generally above window 44. Likewise, in FIG. 21 when apparatus 30 is transferred to the left wrist of the wearer, platform 34 is moved laterally 36 such that it generally overlies window 46 (window 46 not visible in FIG. 21). Thus it can be seen that by allowing platform 34 to slide laterally 36, the same apparatus 30 can be used to accommodate the right or the left wrist of a wearer.

In order to maneuver platform 34 from the right use position (shown in FIG. 4) to the left hand use position, (FIG. 21) the following action is necessary. Firstly, right wrist release button 56 is depressed thereby disengaging finger 66 from engagement surface 70. This allows platform 34 to be rotated thereby displacing sensor 48 away from window 44 (see FIG. 3). Next, apparatus 30 is transferred to the left hand wrist of the wearer and positioned and secured thereto in the manner which has heretofore been described. Next, platform 34 is slid laterally 36 until sensor 48 is placed generally over window 46. Then, platform 34 is rotated 38 towards window 46 until finger 66 positively engages engagement surface 72 of base portion 32.

In order to provide some measure of protection against inadvertent contact of stress sensor 48, coupling member 54 is prevented from pivoting beyond angular displacement 90 as shown in FIG. 8. Angular displacement 90, need only be made large enough to allow finger access to windows 44, 46 thereby permitting an operator to manually palpate an artery of interest to verify the proper positioning of wrist mount apparatus 30. It is thought that by limiting angular displacement 90, sensor 48 will generally not be exposed to inadvertent contact thereby limiting the risk that sensor 48 will be damaged while it is being laterally displaced from its first use position to its second use position. The manner in which angular displacement 90 is limited, is established by limiting the rotation allowed by rear portion 92 of coupling member 54 (see FIGS. 7 and 8). Accordingly, when angular displacement 90 reaches its maximum allowable travel, rear portion 92 of coupling member 54 contacts upper ridge 94 of base portion 32 and is no longer permitted to rotate any further. The amount of angular displacement 90 which is necessary, is generally determined by the length of resilient engaging finger 66, and the amount of clearance needed to manually palpate the artery of interest through an appropriately positioned window. That is to say, displacement 90 must be sufficient enough to allow coupling member 54 to be slid between first and second use positions without resilient engaging finger 66 contacting any portion of base 32. As can be seen from FIG. 15, displacement 96, is available which is much greater than displacement 90 of FIG. 8. Thus, when coupling member 54 is placed intermediate first and second use positions (see FIG. 7), upper ridge 94 cut away 98 is aligned with rear portion 92 thereby removing any interference between rear portion 92 of coupling member 54 and upper ridge 94. This intermediate position where displacement 96 is available, is generally thought to be desirable for the purpose of accessing sensor 48 for calibration and for removing platform 34 from coupling 54. For example, it is contemplated that sensor 48 will be calibrated while it is still mounted to apparatus 30. In this case, a calibration apparatus will directly engage transducer platform 34 for the purpose of calibrating sensor 48 therein. If angular displacement 90 were the only displacement which was permissible, it is generally believed that access to sensor 48, for the purpose of calibration, would be difficult. It is important to note that angular displacement 96 is only achievable when coupling member 54 is placed generally intermediate first and second use positions. This, guarantees that sensor 48 will not be made vulnerable to inadvertent contact during the normal movement which takes place in sliding platform 34 between its first and second use positions.

OVERLOAD RELEASE FEATURE

FIGS. 5A, 5B, 10-14 and FIG. 21 will now be used to describe the overload feature of the present invention. Now referring generally to FIGS. 10 and 11, when maneuvered into its use position, transducer platform 34 is prevented from rotating 38 out from its use position by virtue of the positive engagement between finger 66 and surface 70 of base portion 32. When it is desired to pivot 38 transducer platform 34 away from window 44, button 56 is depressed. Now referring to Figures 10-14, once button 56 is depressed with sufficient inward force, conical surface 74 of right wrist release button 56 engages guide surface 100 of resilient finger 66 thereby causing finger 66 to move off of engagement surface 70 of base 32 (see FIG. 14). This movement of finger 66 causes it to no longer engage surface 70 thereby allowing the upward urging force of spring assembly 80 to cause coupling member 54 to rotate 38. The above-mentioned sequence, of course, takes place when a person using, or administering apparatus 30, wishes to release platform 34 from its use position. However, as is generally disclosed in FIG. 20, it is generally desirable to move 102 sensor 48 upwards and downward 102 so as to achieve flattening of radial artery 104. An applanation apparatus 106 used to achieve flattening of radial artery 104 can be of any number of forms including mechanical, hydraulic, electromechanical or the like. In any event, regardless of which type of applanation apparatus 106 is used to effectuate the movement of sensor 48, there is always a possibility that applanation apparatus 106 will fail in a way which will cause sensor 48 to exert an undesirably high force against tissue 108 covering artery 104. The overload feature of the present invention prevents excessive amounts of force from being applied to tissue 108. FIGS. 10A and 10B will now be used to illustrate this feature of the present invention.

Now referring to FIGS. 10A, 10B and 21, in its normal latching position, finger 66 employs generally horizontal surface 67 to engage generally horizontal engagement surface 70. In the event that apparatus 106 malfunctions and applies excessive amounts of force to tissue 108, width 110 of finger 66 and its material composition can be designed such that, finger 66 bends, or bows, (see FIG. 10B) such that its generally horizontal engaging surface 67 pulls away from generally horizontal surface 70 thereby being urged upwardly by spring assembly 80 and backing sensor 48 away from tissue 108. In a preferred embodiment, generally horizontal surface 67 and generally horizontal surface 70 are made slightly convex with the center 112 of convex surface 67 being slightly displaced 114 from the center 116 of convex surface 70. This displacement 114 between centers 112, 116 of convex surfaces 67, 70 ensures that positive engagement is formed between the two surfaces, but also ensures that once sufficient upward force is exerted by apparatus 106 to cause centers 112, 116 to move slightly past coincidence, an unstable condition exists and the convex curvatures of surfaces 112, 116 will ensure that rapid separation will occur. Thus, the convex nature of the mating surfaces along with the off center arrangement ensures that a positive engagement is made between surfaces 67, 70 during normal operating conditions, and also ensures that when an overload condition is present, quick and sure separation between surfaces 67 and 70 occurs.

ARTERIAL ACCENTUATION AND STABILIZATION FEATURE

Generally referring to FIGS. 10 and 21, because base 32 employs bottom arcuate surface 118, it generally conforms to the contour of a wearers wrist thereby providing some degree of comfort and stability. Moreover, an additional benefit is gained by arcuate 118 surface inasmuch as it tends to prevent lateral movement 120, 122 of artery 104 during the time when apparatus 106 moves 102 sensor 48 into contact with tissue 108. This is an advantage of the present invention inasmuch as any lateral movement 120, 122 of artery 104 during the course of conducting tonometric measurements, tends to decrease the reliability of the data gathered from sensor 48. Thus it can be seen, in contrast with systems which may use generally flat surfaces to engage tissue 108 above artery 104, the arcuate surface of base 32 tends to stabilize artery 104 from lateral movement thereby improving the reliability of the data gathered from sensor 48. Now referring to FIG. 19, radial artery 104 passes under tissue 108. Width 124 of base 32 is relatively narrow compared to width 126 of windows 44, 46. This combination of narrow base portions 32 and wide windows 44, 46 causes radial artery 104 to bulge or become accentuated when base 32 is strapped to the wrist of a wearer. This bulging makes it easier to locate for the operator attempting to palpate artery 104. Thus it can be seen that width 124 of base 32 in general relation to windows 44, 46 acts to accentuate the visibility of artery 104 thereby making it easier to locate.

QUICK DISCONNECT FEATURE

Now referring to FIGS. 5A, 8, 15-18 and 22-24, as was mentioned earlier, it is common to design modular systems so as to make servicing of the system easy to perform. This approach also has the added advantage of generally making the systems separable in a shorter period of time than would otherwise be possible. It is for this reason, that the apparatus of the present invention employs a quick disconnect feature which allows the transducer platform 34 to be readily separated from coupling member 54 should it ever be necessary to replace sensor 48 in the field. This quick disconnect feature of the present invention will now be explained. Now referring to FIG. 5A, as has already been generally discussed, transducer platform 34 is attached to base 32 by way of coupling member 54. Now referring to FIG. 8, when it is desired to remove transducer platform 34 from coupling member 54, finger 66 is released from engaging surface 70 of base portion 32 by depressing button 56 in the manner already described. Next, coupling member 54 is pivoted into displacement 90. Then, coupling member 54 is moved laterally intermediate first and second use positions (see FIG. 6) and again pivoted into angular displacement 96 (see FIG. 15). Now referring to FIG. 15, transducer platform 34 is then forced upwardly 128 thereby disengaging lipped portion 130 of coupling member 54 from depression 132 of transducer platform 34. Likewise, upward force 128 acts to separate cavity 134 of transducer platform 34 from pin 136 of coupling member 54. After this upward movement 128, platform 34 is separable from coupling member 54. Accordingly, should a transducer 48 fail, it is removed from coupling member 54 by virtue of removing its platform 34 from coupling member 54 and a new transducer 48 along with its accompanying platform 34, is coupled to coupling member 54. Thus it can be seen that coupling member 54 can be easily separated from transducer platform 34 to effect quick and easy replacement of transducer 48 in the field. Now referring generally to FIGS. 15-18 and FIGS. 22-24, transducer platform 34 is fitted with recess 138 and coupling member 54 is fitted with dimpled surface 140 such that recess 138 and dimple surface 140 form mating surfaces which act to retain transducer platform 34 to coupling member 54. This retaining action between surfaces 138 and 140 is accomplished by designing a side wall 142 within recess 138. This wall is sized to interfere with the movement of dimple 140 as platform 34 is slid upwardly 128 or downwardly 129. Thus it can be seen that surfaces 138, 140 cooperate to prevent inadvertent separation of platform 34 from coupling member 54. Surfaces 138, 140 are sized such that an upward force 128 of sufficient magnitude is necessary to accomplish the separation of platform 34 from coupling member 54.

ANTICONTAMINATION FEATURE

Now referring to FIG. 21, if the device of the present invention is used on the general public, it may be generally desirable to eliminate the risk of passing contaminants from one wearer to another. Thus, because apparatus 30 is potentially used by many different wearers, it has the potential to transfer contaminants from wearer to wearer by virtue of the direct engagement between sensor 48 with tissue 108. The apparatus of the present invention avoids such transfer of contamination by placing disposable film 144 between tissue 108 and base portion 32. Film 144 is preferably a thin film of elastomer (such as plastic) which is flexible enough not to interfere with the operation of sensor 48. It is also contemplated, that film 144 have at least a portion of one of its surfaces which is adhesive for adhering film 144 to either tissue 108 or base portion 32. Thus, after each use, film 144 is removed and discarded and a new film 144 is installed. Thus, with such a system, the risk of passing contamination from one user to the next or from one user to sensor head 48 is minimized.

Figure 25:
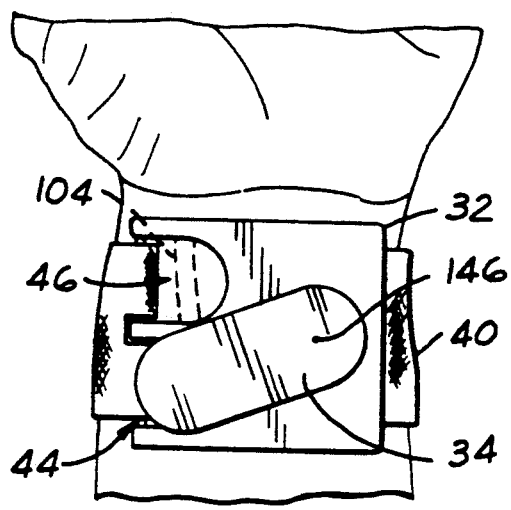
FIG. 25 is a top view of a second embodiment of the wrist mount apparatus of the present invention shown with its transducer platform in a first position.
Figure 26:
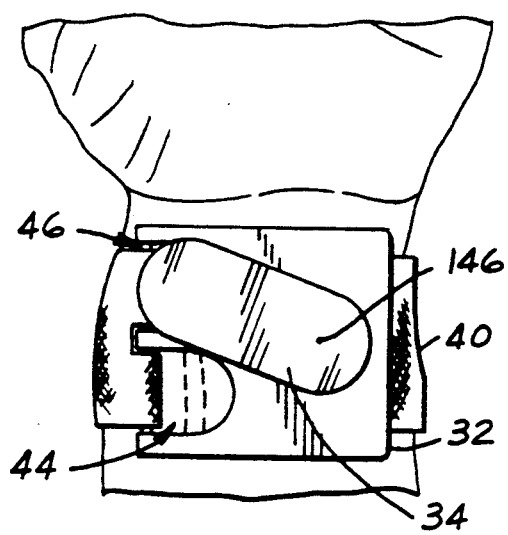
FIG. 26 is the second embodiment of the wrist mount apparatus of the present invention shown with its transducer platform pivoted out of the first position and into a second position.
Figure 27:
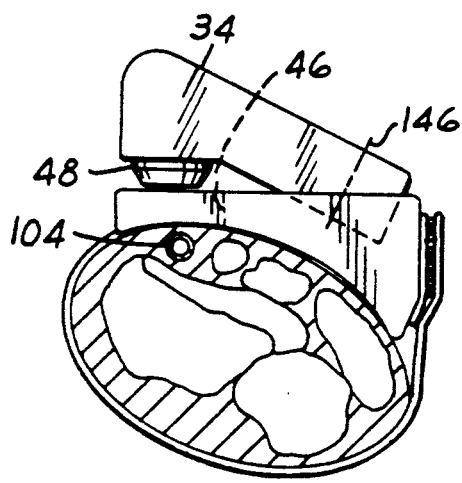
FIG. 27 is a cross-sectional view of the second embodiment of the wrist mount apparatus of the present invention with its sensor head fully retracted.
Figure 28:
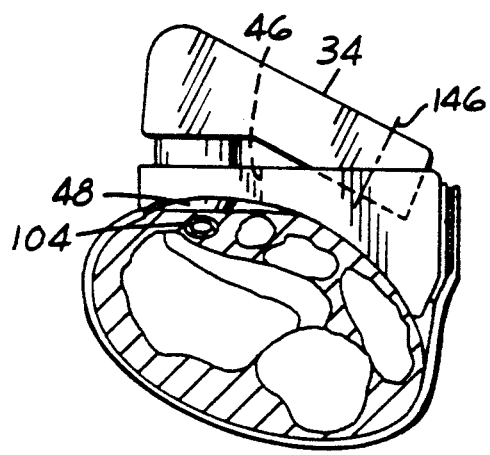
FIG. 28 is a cross-sectional view of the second embodiment of the wrist mount apparatus of the present invention shown with its sensor head in an intermediate position.
Figure 29:
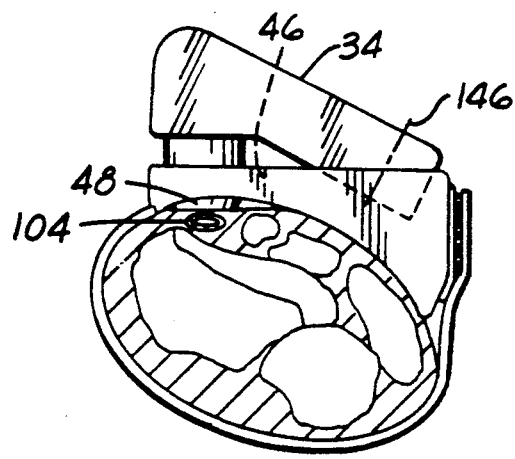
FIG. 29 is a cross-sectional view of the second embodiment of the wrist mount apparatus of the present invention shown with its sensor head in a fully extended position.

Now referring to FIG. 25, a second embodiment of the wrist mount apparatus of the present invention is shown having base 32 attached to a wrist of a wearer via restraining strap 40. Base 32 and restraining strap 40 function in the identical way which has heretofore been described in conjunction with the first embodiment. The primary difference between the first and second embodiment lies in the manner in which transducer platform is moved from its first position to its second position thereby being switched between windows 44, 46 respectively. As was mentioned in conjunction with the first embodiment, transducer platform 34 in that embodiment, is adapted to move between windows 44, 46 by way of lateral movement along coupling retaining pin 55. In contrast to that method, in the second embodiment, transducer platform 34 is adapted to move between windows 44, 46 by way of pivoting about axis 146 by way of internal pivot mechanism (not shown). Accordingly, it can be seen in conjunction with FIGS. 25 and 26, that when the second embodiment of the wrist mount apparatus of the present invention is fastened to the wrist of a wearer, and transducer platform 34 is positioned over first window 44 (see FIG. 25), artery 104 can be palpated through window 46 to ensure that base 32 is properly positioned. After manual palpation takes place, transducer platform 34 is pivoted about axis 146 to thereby position sensor head (sensor head not shown) over window 46. It is seen in conjunction with FIGS. 27 through 29 that once sensor 48 is positioned over window 46, it can be passed through window 46 thereby contacting the tissue directly over radial artery 104. As sensor 48 is depressed into the tissue overlying radial artery 104, radial artery 104 will applanate. Thus it can be seen, in conjunction with FIGS. 25 through 29, that the second embodiment of the present invention is effective for operating on either the right or the left wrist of a wear and also effective for positioning a sensor over any artery of interest for the purpose of applanating the artery.

The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. Accordingly, it is to be understood that the subject matter sought to be afforded protection hereby should be deemed to extend to the subject matter defined in the appended claims, including all fair equivalents thereof.

I claim:

1. A wrist mount apparatus for mounting a tissue stress transducer on either wrist of a wearer in operative engagement with the tissue overlying an artery of interest, said artery including a longitudinal axis along its length, said wrist mount apparatus comprising:

wrist mount means for grasping a wrist of said wearer in proximity to the said artery of interest, a base portion coupled to said wrist mount means, a transducer platform including means for housing said tissue stress transducer, parallel coupling means including a first end connected to said transducer platform and second end cooperatively engaged to said base portion for moving said transducer platform between first and second positions generally parallel to said longitudinal axis of said artery of interest, whereby said wrist mount apparatus is adapted to mount to the right wrist of the wearer, and said parallel coupling means is operative for moving said transducer platform generally parallel to said longitudinal axis of said artery into said first position, thereby enabling said transducer platform to place said tissue stress sensor into operative engagement with the tissue overlying an artery of interest in said wearer's right wrist, and whereby said wrist mount apparatus is adapted to mount to the left wrist of the wearer, and said parallel coupling means is operative for moving said transducer platform generally parallel to said longitudinal axis of said artery into said second position thereby enabling said transducer platform to place said tissue stress sensor into operative engagement with the tissue overlying an artery of interest in said wearer's left wrist, whereby said apparatus is adapted for use on the right or left wrist of the wearer.

2. The wrist mount apparatus of claim 1, wherein said parallel coupling means further includes means for pivoting said transducer platform generally about said longitudinal axis of said artery of interest.

3. The wrist mount apparatus of claim 2, further including locking means attached between said base portion and said transducer platform for opposing said transducer platform from freely pivoting generally about said longitudinal axis of said artery of interest.

4. The wrist mount apparatus of claim 3, wherein said locking means further includes releasing means attached to said base portion for releasing said locking means thereby allowing said platform to be freely pivoted generally about said longitudinal axis of said artery of interest.

5. The wrist mount apparatus of claim 4, wherein said releasing means further includes urging means for pivoting said transducer platform generally about an axis parallel to said longitudinal axis of said artery of interest thereby displacing said locking means from said locking position to prevent said locking means from being operative upon the disengagement of said releasing means.

6. The wrist mount apparatus of claim 3, wherein said parallel coupling means further includes means for confining the pivotal movement of said transducer platform to a first angular displacement when said transducer platform is disposed in at least one of said first and second positions, and means for confining the pivotal movement of said transducer platform to a second angular displacement when said transducer platform is disposed at a third position wherein said second angular displacement is greater than said first angular displacement thereby providing unfettered access to said tissue stress transducer during a calibration of said tissue stress transducer.

7. The wrist mount apparatus of claim 6, wherein said third position is intermediate said first and second positions.

8. The wrist mount apparatus of claim 1, wherein said base portion includes first and second window portions for passing said transducer therethrough, said first window portion for placing over an artery of interest when said base portion is placed on the right wrist of the wearer proximate said artery of interest and said second window portion for placing over an artery of interest when said base portion is placed on the left wrist of the wearer proximate said artery of interest.

9. The wrist mount apparatus of claim 1, wherein said wrist mount means further includes a flexible strap for fixing said base portion to the wrist of the wearer.

10. The wrist mount apparatus of claim 1, wherein said base portion has a wrist engaging surface wherein said wrist engaging surface is generally concave thereby generally conforming to the natural curvature of the wearers wrist in the area engaged by said base portion.

11. The wrist mount apparatus of claim 1, wherein said parallel coupling means includes means for allowing said transducer platform to be freely pivoted about an axis which is generally perpendicular to said longitudinal axis of said artery of interest.

12. A wrist mount apparatus for placing a tissue stress transducer in operative engagement with the tissue overlying an artery of interest, said wrist mount apparatus comprising:

a base portion including means for mounting said base portion to the wrist of the wearer, a transducer platform including means for housing said tissue stress transducer, said transducer platform including means for movably engaging said transducer platform to said base portion, forcing means, coupled to said transducer platform and including means for engaging said tissue stress transducer, for forcing said tissue stress transducer into operative engagement with said tissue overlying said artery of interest, force sensing means, coupled between and sensitive to a force between said base portion and said transducer platform, for allowing said transducer platform to move away from said base portion thereby releasing said tissue stress transducer from operative engagement with said tissue overlying said artery of interest whenever said force of said tissue stress transducer against the tissue of the wearer exceeds a predetermined value.

13. The wrist mount apparatus of claim 12, wherein said force sensing means includes a resilient engaging finger extending from said transducer platform and said base portion includes an engaging surface, said finger including means for engaging said engaging surface of said base portion thereby retaining said transducer platform to said base portion and preventing relative movement between said base portion and said transducer platform, whereby when force of sufficient urging is exerted by said tissue stress sensor against the tissue overlying said artery of interest, said resilient engaging finger is distorted to disengage from said engaging surface of said base portion, thereby allowing relative movement to take place between said base portion and said transducer platform.

14. The wrist mount apparatus of claim 13, wherein said resilient engaging finger includes a convex engaging surface, and wherein said engaging surface of said base portion is generally convex.

15. A wrist mount apparatus for placing a tissue stress transducer in operative engagement with the tissue overlying an artery of interest, said wrist mount apparatus comprising:
- a base portion including means for mounting said base portion to the wrist of the wearer,
- a transducer platform including means for engaging said tissue stress transducer,
- quick disconnect means for connecting said transducer platform to said base portion, whereby said disconnect means allows said transducer platform and said tissue stress sensor to be quickly removed from said base portion,
- wherein said quick disconnect means includes a coupling member fastened to said base portion, wherein said coupling member includes a lipped portion and said transducer platform includes a recessed portion, wherein said lipped portion cooperatively engages and retains said recessed portion, wherein said coupling member includes a retaining pin and said transducer platform includes a receiving cavity, said retaining pin positioned on said coupling member to be received within said receiving cavity as said lipped portion of said coupling member is slidingly engaged with and retained within said recessed portion of said transducer platform.

16. The wrist mount apparatus of claim 15, wherein said coupling member and said transducer platform both include interference fit surfaces, wherein said interference fit surfaces contact and pass beyond one another as said lipped portion of said coupling member is slidingly engaged with said recessed portion of said transducer platform, said interference fit surfaces thereby resisting the separation of said coupling member from said transducer platform.

17. The wrist mount apparatus of claim 16, wherein said interference fit surfaces include cooperatively mating contours.

* * * * *